United States Patent [19]

Takahashi

[11] Patent Number: 4,580,885
[45] Date of Patent: Apr. 8, 1986

[54] APPARATUS AND METHOD FOR DETERMINING EXPOSURE CONDITION OF OPHTHALMIC PHOTOGRAPHING

[75] Inventor: Susumu Takahashi, Tokyo, Japan

[73] Assignee: Tokyo Kogaku Kikai Kabushiki Kaisha, Tokyo, Japan

[21] Appl. No.: 650,902

[22] Filed: Sep. 14, 1984

[30] Foreign Application Priority Data

Sep. 20, 1983 [JP] Japan .............................. 58-173636

[51] Int. Cl.[4] .......................... G03B 29/00; A61B 3/14
[52] U.S. Cl. ........................................ 354/62; 354/432
[58] Field of Search .................................. 354/432, 62

[56] References Cited

U.S. PATENT DOCUMENTS

| | | | |
|---|---|---|---|
| 4,264,153 | 4/1981 | Ito | 354/62 |
| 4,306,787 | 12/1981 | Fukuhara et al. | 354/432 |
| 4,394,078 | 7/1983 | Terashita | 354/432 |
| 4,445,778 | 5/1984 | Nakauchi | 354/432 |
| 4,476,383 | 10/1984 | Fukuhara et al. | 354/432 |

Primary Examiner—Russell E. Adams
Attorney, Agent, or Firm—Brumbaugh, Graves, Donohue & Raymond

[57] ABSTRACT

An ophthalmic photographing apparatus for determining the exposure condition of ophthalmic photographs, includes an illuminating optical system for illuminating a subject to be photographed, a photographing optical system for photographing the subject, an exposure control system comprising light detecting means for detecting intensities of light reflected at a plurality of zones of the subject, boundary level setting means for dividing a region between the highest and lowest values of the light intensities detected by the detecting means into a plurality of sub-regions and determining a boundary value between each two adjacent sub-regions, exposure condition setting means for setting a selected one of the sub-regions, comparator means for comparing output of the detecting means with the boundary value related to the selected sub-region to thereby select the outputs included in the selected sub-region, and exposure control means for controlling exposure in accordance with the selected outputs of the detecting means.

A method for determining exposure condition of ophthalmic photographing comprising the steps of detecting intensities of light reflected at a plurality of zones in a subject to be photographed, dividing a region between highest and lowest values of the detected light intensities into a plurality of sub-regions, selecting one of the sub-regions and extracting the detected light quantities included in the selected sub-region, calculating a mean value of the extracted light intensities, and determining the exposure in accordance with the mean value of the extracted light quantities.

6 Claims, 5 Drawing Figures

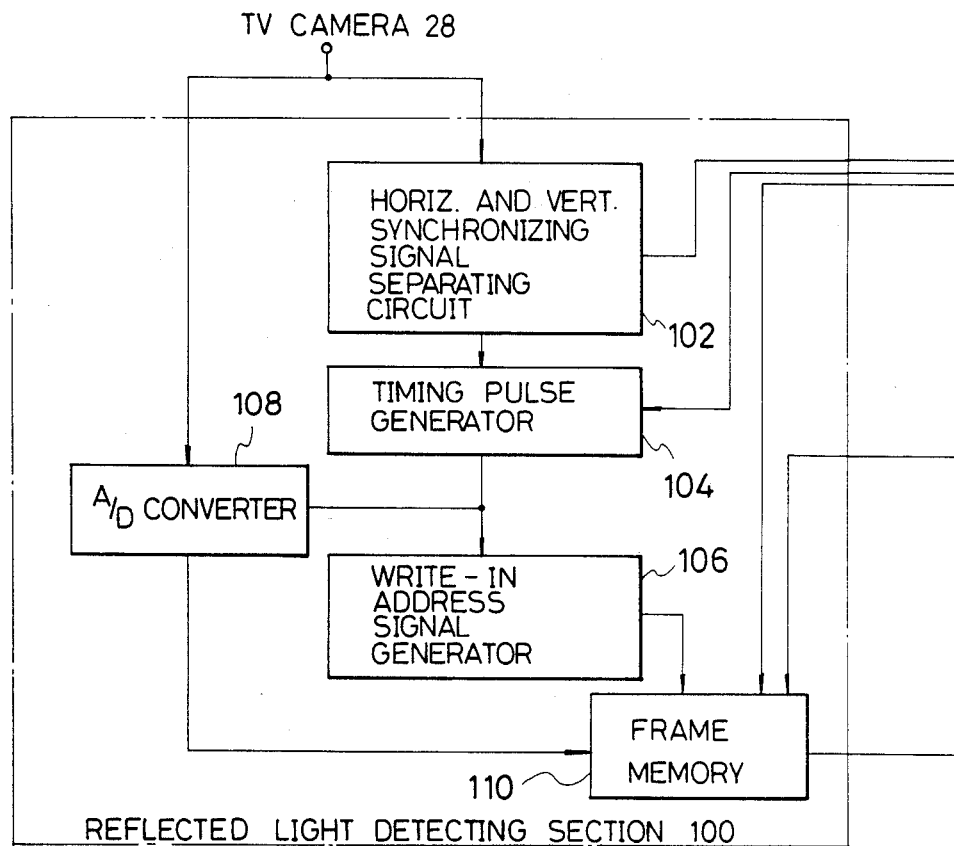

APPARATUS AND METHOD FOR DETERMINING EXPOSURE CONDITION OF OPHTHALMIC PHOTOGRAPHING

BACKGROUND OF THE INVENTION

1. Field of the Invention

The present invention relates to an ophthalmic photographing apparatus and more particularly to an exposure control therefore. More specifically, the present invention pertains to an exposure control system for an ophthalmic photographing apparatus wherein the exposure is determined so that a desired extent of exposure is established at a desired part of an ophthalmic subject to be photographed.

2. Description of Prior Art

In a conventional ophthalmic photographic instrument, for example, an eye fundus camera, the exposure for photographing is generally determined by detecting an overall quantity of light reflected at the retina of a patient's eye by means, for example a CdS detector. In other words, the exposure is determined in accordance with an average quantity of light beams from various parts of the eye retina. It should however be noted that the retina is constituted by various parts of different reflectivities, such as a disk, a network of blood vessels, a yellow spot, and the like so that the picture taken under the exposure determined as described above usually includes portions of under-exposure as well as portions of over-exposure. This very often causes serious problems in photographing diseased eyes because precise photographic records of diseased portions are particularly critical for determining curative treatment.

DESCRIPTION OF THE INVENTION

Object of the Invention

It is an object of the present invention to provide means and method in an ophthalmic photographing for determining exposure appropriate for a desired portion, for example, a diseased portion of an ophthalmic subject.

Another object of the present invention is to provide an ophthalmic photographing apparatus having an exposure control system which can determine the exposure so that a desired portion of an ophthalmic subject can be photographed with an appropriate exposure.

SUMMARY OF THE INVENTION

According to the present invention, the above and other objects can be accomplished by an ophthalmic photographing apparatus including an illuminating optical system for illuminating a subject to be photographed, a photographing optical system for photographing the subject, an exposure control system comprising light detecting means for detecting intensities of lights reflected at a plurality of zones of the subject, boundary level setting means for dividing a region between a highest and lowest values of the light intensities detected by the detecting means into a plurality of sub-regions and determining a boundary value between each two adjacent sub-regions, exposure condition setting means for setting a selected one of said sub-regions, comparator means for comparing outputs of said detecting means with the boundary value related to the selected sub-region to thereby select the outputs included in the selected sub-region, and exposure control means for controlling exposure in accordance with the selected outputs of the detecting means. In one mode of the present invention, the region between the highest and lowest values of the light quantities is divided into three equal sub-regions by setting two boundary values. The exposure control means may include a mean value of the selected outputs of the detecting means.

In one aspect of the present invention, the illuminating optical system has a photographing light source and an observing light source, and the exposure is determined while the observing light source is in operation. There may be a change or fluctuation of the intensity of illumination light from the observing light source, and the aforementioned mean value of the selected outputs may be affected by such change or fluctuation of the intensity of the illumination light. In order to avoid this problem, the exposure control means may be provided with compensating means for modifying the outputs of the comparator means so that the change or fluctuation of the light source be compensated for.

According to the present invention, there is also provided a method for determining exposure condition of ophthalmic photographing comprising steps of detecting intensities of lights reflected at a plurality of zones in a subject to be photographed, dividing a region between highest and lowest values of the detected light intensities into a plurality of sub-regions, selecting one of the sub-regions and extracting the detected light quantities included in the selected sub-region, calculating a mean value of the extracted light intensities, and determining the exposure in accordance with the mean value of the extracted light quantities

BRIEF DESCRIPTION OF THE DRAWINGS

FIGS. 2, 2A and 2B are block diagrams of a signal processing system adopted in the embodiment of the present invention; and, FIG. 3 is a circuit diagram of an illumination control circuit.

DESCRIPTION OF THE PREFERRED EMBODIMENT

Figure 1:
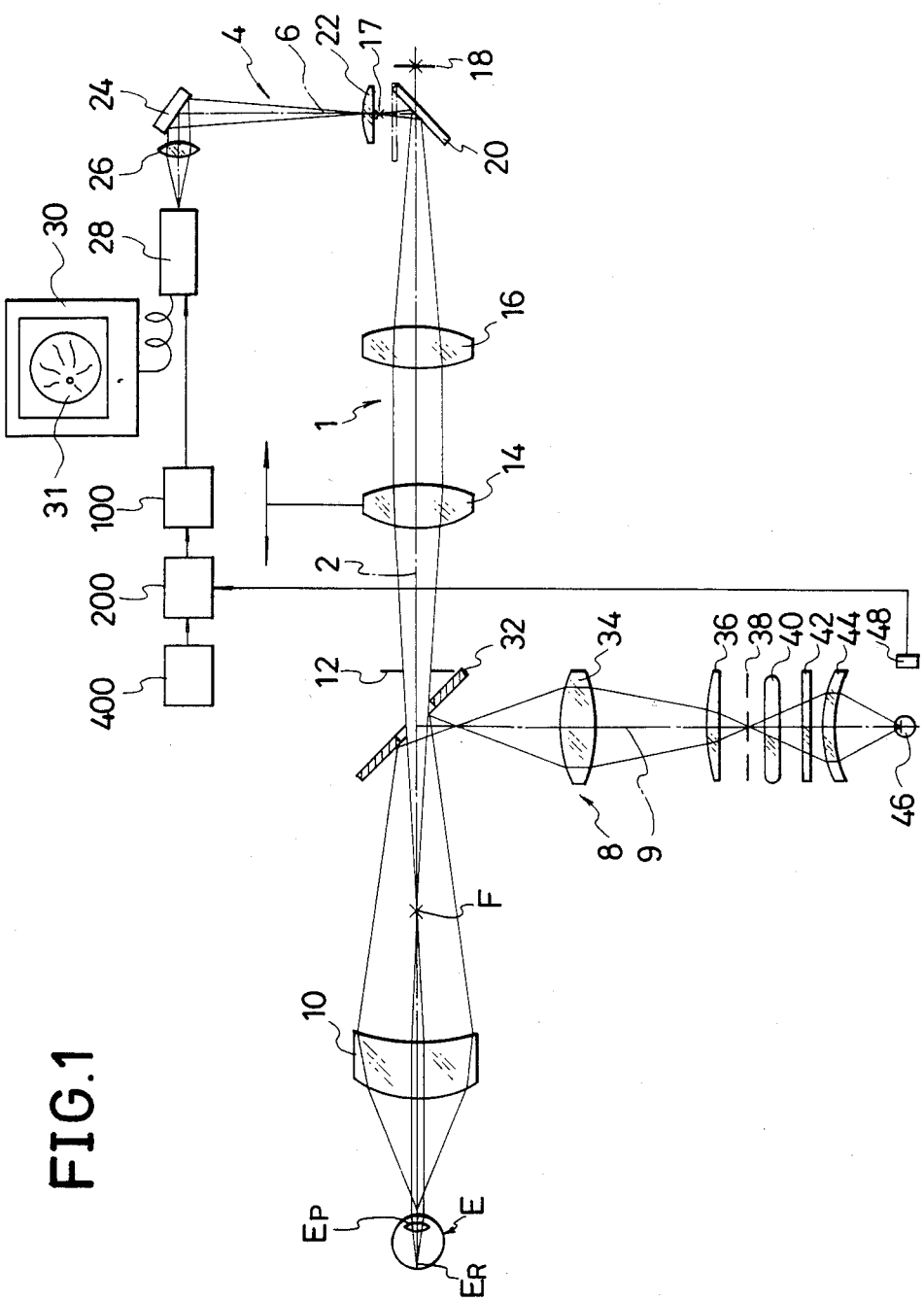
FIG. 1 is a diagrammatical illustration of an optical system of an eye fundus camera in which the present invention is embodied.

Referring now to the drawings, there is shown an eye fundus camera which includes an optical system, a signal processing system, and a lighting control system.

The optical system, as shown in FIG. 1, has a photographing optical system 1 for photographing a retina $E_R$ of an eye E, an illuminating optical system 8 for illuminating the retina $E_R$ for observation and photographing, and a finder system 4 for observing the retina on TV.

The photographing optical system 1 comprises an objective lens 10 having an optical axis 2 and adapted to be placed opposite to the eye E. On the optical axis 2 of the objective lens 1, there is an aperture plate 12 located conjugate with the pupil $E_P$ of the eye E with respect to the objective lens 1. The photographing optical system 1 further includes a focusing lens 14, an imaging lens 16 and a photographing film 18 which are arranged in this order along the optical axis 2 of the objective lens 10. Although not shown in FIG. 1, there is provided a shutter in front of the photographing film 18. The lenses 14 and 16 are arranged so as to form an afocal optical system. The focusing lens 14 is adapted to be moved along the optical axis 2 in order to produce an image of the retina $E_R$ at F and then at the film 18.

The illuminating optical system 8 includes an observation light source 46 and a photographing light source 40. Between the observation light source 46 and the photographing light source 40, there is located a condenser lens 44 and a heat-blocking filter 42. The light from anyone of the light sources 40 and 46 is passed through a ring-shaped aperture of an aperture plate 38, and then through a condenser lens 36 and a relay lens 34 along an illuminating optical axis 9 which intersects the optical axis 2. On the optical axis 2, there is obliquely provided an apertured mirror 32 which is substantially conjugate with the pupil $E_P$. The illuminating light which has passed through the ring-shaped aperture of the aperture plate 38 produces an image of the ring-shaped aperture on the reflective surface of the mirror 32 and reflected toward the eye E to form an image of the ring-shaped aperture in the pupil $E_P$ and then illuminates the retina $E_R$.

The finder system 4 includes a retractable mirror 20 obliquely provided in front of the film 18. Along the reflecting optical path of the mirror 20, there is a field lens 22 which is provided on an image plane substantially conjugate with the photographing film 18. The light beam which has passed through the imaging lens 16 is therefore reflected by the mirror 20 to produce an image of the retina $E_R$ on the field lens 22. The image is then relayed through a mirror 24 and an imaging lens 26 to a photoelectric surface of a TV camera 28 which produces a signal for producing a visible image 31 of the retina $E_R$ on a monitor TV 30.

In operation of the optical system mentioned above, the retina $E_R$ is illuminated by the beams of illumination light from the illuminating light sorce 46 which is projected through the objective lens 10. The light beams are reflected at the retina $E_R$ and passed again through the objective lens 10 along the optical axis 2. The light beams which have passed through the lenses 14 and 16 are reflected by the retractable mirror 20 positioned as shown in FIG. 1 to form an image of the retina on the field lens 22. The retina image on the field lens 22 is relayed to the TV camera 28 so that a visible image 31 of the retina $E_R$ is produced on the monitor TV 30.

For focusing the optical system, the focusing lens 14 is moved along the optical axis 2 while watching the visible image 31 on the monitor TV 30. For photographing, the mirror 20 is retracted to the position shown by a phantom line in FIG. 1, the shutter is released and the photographing light source 40 is fired so that the image of the retina $E_R$ is projected on the film 18. In order to control the exposure for photographing by determining the time of energization of the light source 40, there is provided an exposure control system.

Figure 2B:
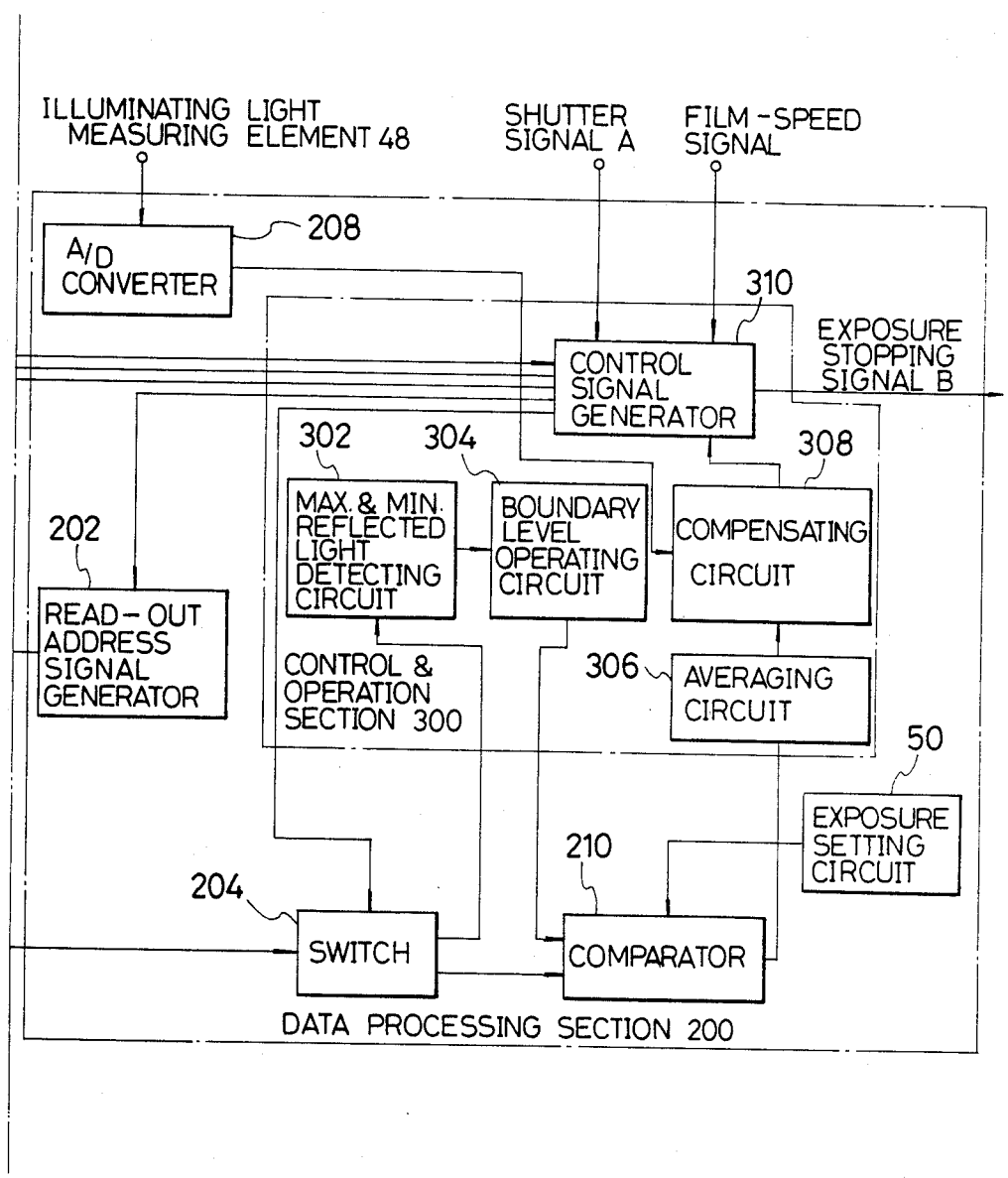

Referring now to FIG. 2, there is shown in block diagram a signal processing circuit which constitute a part of the exposure control system. The signal processing circuit consists of a reflected light detecting section 100 and a data processing section 200 including a control and operation section 300.

The reflected light detecting section 100 functions to detect the quantity of light reflected at the retina $E_R$ in terms of the output of the TV camera 28. The detecting section 100 includes a horizontal and vertical synchronizing signal separating circuit 102, a timing pulse generator 104, a write-in address signal generator 106, an A/D converter 108, and a frame memory 110.

The horizontal and vertical synchronizing separating circuit 102 is connected with the TV camera 28 to receive the output signal therefrom and functions to separate the output signal of the TV camera 28 into horizontal synchronizing signals and vertical syncronizing signals, which are respectively applied to the timing pulse generator 104 and a control signal generator 310 which will be described later. The timing pulse generator 104 has an output connected with the write-in address signal generator 106 and the A/D converter 108. The generator 104 starts to generate timing pulses based on the horizontal synchronizing signals received from the circuit 102, when a pulse generator start signal is applied from the control signal generator 310. It will therefore be understood that the timing pulses are synchronous with the output of the TV camera 28.

The write-in address signal generator 106 has an output connected with the frame memory 110. A write-in address signal produced by the generator 106 in accordance with the timing pulses is applied to the frame memory 110. The A/D converter 108 has an input connected with the TV camera 28 and an output connected with the frame memory 110. The A/D converter 108 functions to convert the analogue output of the TV camera 28, namely signals corresponding to the intensity of light reflected at the retina $E_R$ into a digital signal. The digital output of the A/D converter 108 is applied to the frame memory 110. The frame memory 110 functions to memorize the outputs of the A/D converter 208 one by one in accordance with the write-in address signals.

The data processing section 200 includes an operation section 300, a read-out address signal generator 202, a switch 204, an exposure setting circuit 50, an A/D converter 208, and a comparator 210. The section 200 functions to generate an exposure control signal in accordance with the output of the frame memory 110.

The operation section 300 includes a highest and lowest light detecting circuit 302, a boundary level operating circuit 304, an averaging circuit 306, a compensating circuit 308, and the previously mentioned control signal generator 310. The section 300 functions to process the output of the reflected light detecting section 100 so as to generate an exposure control signal.

The read-out address signal generator 202 has an input connected with the control signal generator 310 and an output connected with the frame memory 110 which has an output connected with the switch 204. The output of the signal generator 202 produced in accordance with the output of the generator 310 is applied to the frame memory 110 so that the data memorized by the frame memory 110 are applied to the switch 204 one by one.

The switch 204 has an input connected with the control signal generator 310 and outputs connected respectively with the comparator 210 and the detecting circuit 302. The switch 204 functions to pass the output of the frame memory 110 alternately to the comparator 210 and the highest and lowest reflected light detecting circuit 302.

The exposure setting circuit 50 is connected with the comparator 210, and applies to the comparator 210 a command regarding the zone of the retina $E_R$ which is particularly to be investigated or any other type of command necessary for determining the exposure condition. The setting means of the exposure setting circuit 50, for example, may be a switch having portions corresponding to a bright, medium and dark zones in the retina, or a disease selecting switch which may select the portions on the retina $E_R$ to be investigated. The exposure condition signal as applied by the exposure setting circuit 50 to the comparator 210 functions to determine the reference level of the comparator 210. It is preferred that the circuit 50 produces a binary signal as the exposure condition signal.

The highest and lowest reflected light detecting circuit 302 has an input connected with the switch 204 and an output connected with the boundary level operating circuit 304. The circuit 302 functions to detect the highest and lowest values of the signals which have passed from the frame memory 110 through the switch 204 and produce a highest and lowest signals which are applied to the boundary level operating circuit 304.

The boundary level operation circuit 304 calculates the boundary levels corresponding to the exposure condition set by the exposure setting circuit 50 in accordance with the output of the detecting circuit 302. In case where the data of the highest and lowest values of the light intensity detected by the detecting circuit 302 are represented by V max and V min respectively and that the retina $E_R$ is divided into three zones of different reflectivity, namely, a bright, medium and dark zones, the upper and lower boundary levels $V_{SU}$ and $V_{SL}$ are calculated by the following equations, $$V_{SU} = \tfrac{2}{3}(V_{max} - V_{min}) + V_{min} = \tfrac{2}{3}V_{max} + \tfrac{1}{3}V_{min}$$

$$V_{SL} = \tfrac{1}{3}(V_{max} - V_{min}) + V_{min} = \tfrac{1}{3}V_{max} + \tfrac{2}{3}V_{min}$$

The signal of levels $V_{SU}$ and $V_{SL}$ is applied to the comparator 210.

The comparator 210 has an output connected with the averaging circuit 306. The comparator 210 compares signals from the frame memory 110 with the upper boundary level $V_{SU}$ and the lower boundary level $V_{SL}$ calculated by the boundary level operating circuit 304. The exposure condition signal as applied by the exposure setting circuit 50 is used to determine as to whether the signals from the frame memory 110 lower than the value $V_{SL}$, between the value $V_{SL}$ and $V_{SU}$ or higher than $V_{SU}$ be passed to the averaging circuit 306. For example, when the dark zone is selected by the circuit 50, the signals from the frame memory lower than the value $V_{SL}$ are passed. When the medium zone is selected, signals between the values $V_{SL}$ and $V_{SU}$ are passed. Similarly, when the bright zone is selected, signals higher than the value $V_{SU}$ are passed to the circuit 306. The averaging circuit 306 calculates a mean value of the signals received from the comparator 210 and applies an output to the compensating circuit 308.

As shown in FIG. 1, there is provided a detecting element 48 so as to detect the intensity of light from the light source 46. The output of the detecting element 48 is connected with the A/D converter 208 which has an output connected to the compensating circuit 308.

The intensity of the light emitted from the light source 46 may change depending on the condition of the power source or the life history of the light itself, and such change may affect the level of the output of the averaging circuit 306. The compensating circuit 308 functions to compensate for such change in the intensity of light from the light source 46. Assuming that Va means the output of the averaging circuit 306, $L_1$ means the output of the A/D convertor 208, and Lo means the predetermined intensity of illuminating light from the light source 46, the compensating circuit 308 produces a signal of a value Vo calculated by the following equation.

$$V_o = \frac{L_o}{L_1} V_a$$

The output of the compensating circuit 308 is applied to the control signal generator 310.

The control signal generator 310 further receives a film speed signal A and a shutter release signal and calculates the exposure time in accordance with the value Vo and the film-speed signal. The exposure time starts upon shutter release which is initiated by a depression of a shutter release button at which time, the photographing light source 40 is fired. The control signal generator 310 calculates the exposure time in accordance with the signal from the compensating circuit 308 and produces an exposure stopping signal B upon expiry of the exposure time. The signal B is then applied to the illuminating control circuit 400.

The generator 310 is connected with the frame memory 110, and a clear signal is applied from the generator 310 to the frame memory 110 at every predetermined time intervals so that the memory of the frame memory 110 is cleared.

The generator 310 is also connected with the switch 204 to apply a switching signal to the switch 204 when the frame memory 110 has memorized a set of data to have the switch 204 function to direct the output of the frame memory 110, at first, to the detecting circuit 302, and then to the comparator 204 after the comparator 210 has received the boundary level signals from the circuit 304. The generator 310 is also connected with the read-out address signal generator 202 to apply a start signal which is used for generating the read-out address signal for the frame memory 110.

Figure 3:
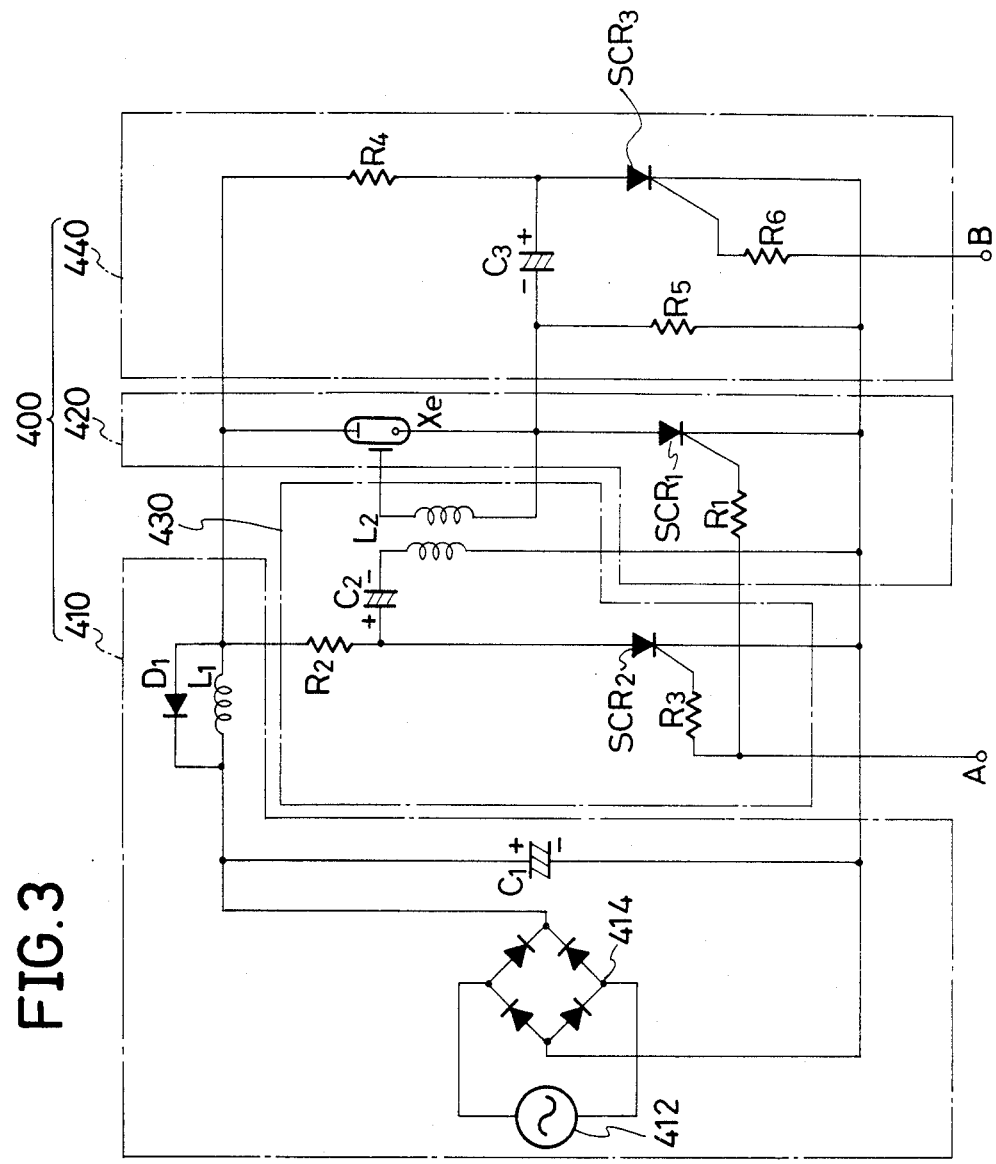

Referring now to FIG. 3, there is shown an electric circuit 400 for controlling the photographing light source 46, auch as a xenon flash tube Xe in accordance with the shutter signal A and the exposure stopping signal B. The circuit 400 consists of a power section 410, a lighting section 420, a trigger section 430, and a current converting section 440.

The power section 410 includes a diode bridge 414 connected with a AC power unit 412, a main capacitor $C_1$ connected in parallel with the diode bridge 414, and a parallel circuit of a diode $D_1$ and a coil $L_1$ connected with the main capacitor $C_1$. AC voltage from the AC power unit 412 is converted into DC voltage by the diode bridge 414 and applied to the main capacitor $C_1$ to be charged therein. The DC voltage charged in the main capacitor $C_1$ is applied to the lighting section 420 and the current converting section 440 through the parallel circuit of the diode $D_1$ and the coil $L_1$.

The main capacitor $C_1$ supplies a current enough to light the xenon flash tube Xe, and its capacity depends on the amount of radiation of the tube Xe. The coil $L_1$ controls an instantaneous current and the diode $D_1$ prevents a back-rush of the current.

The lighting section 420 includes the aforementioned xenon flash tube Xe, a thyristor $SCR_1$ connected with the tube Xe in series, and a resistor $R_1$ connected with the gate of the thyristor $SCR_1$. The gate of the thyristor $SCR_1$ receives the shutter signal A through the resistor $R_1$. When the shutter release button is depressed, the thyristor $SCR_1$ turns "on" so that the voltage from the power section 410 is supplied to the tube Xe.

The trigger section 430 includes a coil $L_2$, a capacitor $C_2$ connected with the coil $L_2$, a resistor $R_2$ connected with the resistor $R_2$ and the coil $L_1$, a thyristor $SCR_2$ connected with the resistor $R_2$ and the capacitor $C_2$, and a resistor $R_3$ connected with the gate of the thyristor $R_3$. One of the secondary terminals of the coil $L_2$ is connected with the trigger electrode of the tube Xe. The trigger section 430 functions to produce a high voltage for starting radiation of the tube Xe corresponding to the shutter signal A. Before the shutter signal A is supplied to the thyristors $SCR_1$ and $SCR_2$ through the resistors $R_1$ and $R_3$, the thyristor $SCR_2$ is "off" and the capacitor $C_2$ is charged in polarity shown in FIG. 3 through the resistor $R_2$ and the coil $L_2$. After the shutter signal A is supplied to the thyristor $SCR_1$ and $SCR_2$ through the resistors $R_1$ and $R_3$, the thyristors $SCR_1$ and $SCR_2$ turn "on" so that a circuit is established across the capacitor $C_2$, and a current is produced through the primary winding of the coil $L_2$. Thus, a high voltage is produced in the secondary winding and applied to the trigger electrode and the cathode of the tube Xe. The tube Xe therefore starts to fire since the thyristor $SCR_1$ is already turned "on".

The current inverting section 440 includes a capacitor $C_3$, resistors $R_4$ and $R_5$ connected with the capacitor $C_3$, a thyristor $SCR_3$ connected with the resistor $R_4$ and the capacitor $C_3$, and a resistor $R_6$ connected with the gate of the thyristor $SCR_3$. The resistance value of the resistor $R_4$ is determined so as to make the current passing through the resistor $R_4$ be less than that required for holding the thyristor $SCR_3$ "on", when the voltage is supplied to the resistor $R_4$ from the power section 410. The value of the resistor $R_5$ is determined in accordance with the charging time of the capacitor $C_3$.

The capacitance of the capacitor $C_3$ is determined to make the current passing through the thyristor $SCR_1$ to invert so that the thyristor $SCR_1$ is turned "off" by a voltage of opposite polarity.

Under the constitution mentioned above, before the shutter release button is depressed, the capacitor $C_3$ is charged in the plorarity shown in FIG. 3 since the thyristors $SCR_1$ and $SCR_3$ are "off". When a predetermined time is passed after the firing of the tube Xe, or in other words, when the film is sufficiently exposed, the exposure stopping signal B is supplied from the control and operation section 300 through the resistor $R_6$ to the thyristor $SCR_3$. Thus, the thyristor $SCR_3$ is turned "on", so that the capacitor $C_3$ is grounded at the electrode connected with the thyristor $SCR_3$. Then, the current passing through the thyristor $SCR_1$ is directed to the capacitor $C_3$, and the thyristor $SCR_1$ is subjected to a voltage of opposite polarity so that the thyristor $SCR_1$ is turned "off". The capacitor $C_3$ is then gradually charged in the polarity opposite to the one shown in FIG. 3, so that the current is finally prevented from flowing through the tube Xe so that the tube Xe is de-energized.

When the tube Xe is de-energized, the thyristor $SCR_3$ is turned "off" since the resistor $R_4$ has the previously mentioned resistance value. The capacitor $C_3$ is charged in the polarity opposite to the one shown in FIG. 3 when the tube Xe is de-energized but it is thereafter charged in the polarity shown in FIG. 3. The electric circuit 400 therefore restores its original condition.

The invention has thus been shown and described with reference to a specific embodiment, however, it should be noted that the invention is in no way limited to the details of the illustrated arrangements but changes and modifications may be made without departing from the scope of the appended claims.

I claim:

1. An ophthalmic photographing apparatus including an illuminating optical system for illuminating a subject to be photographed, a photographing optical system for photographing the subject, an exposure control system comprising light detecting means for detecting intensities of lights reflected at a plurality of zones of the subject, boundary level setting means for dividing a region between a highest and lowest values of the light intensities detected by the detecting means into a plurality of sub-regions and determining a boundary value between each two adjacent sub-regions, exposure condition setting means for setting a selected one of said sub-regions, comparator means for comparing outputs of said detecting means with the boundary value related to the selected sub-region to thereby select the outputs included in the selected sub-region, and exposure control means for controlling exposure in accordance with the selected outputs of the detecting means.

2. An apparatus in accordance with claim 1 in which the region between, highest and lowest values of the light intensities is divided into three equal sub-regions by setting two boundary values.

3. An apparatus in accordance with claim 1 in which the exposure control mean is controlled in accordance with a mean value of the selected outputs of the detecting means.

4. An apparatus in accordance with claim 1 in which the illuminating optical system has a photographing light source and an observing light source and the exposure is determined while the observing light source is in operation.

5. An apparatus in accordance with claim 1 in which the exposure control means is provided with compensation means for modifying any outputs of the comparator means so that the change or fluctuation of the light source be compensated for.

6. A method for determining exposure condition of ophthalmic photographing comprising steps of detecting intensities of lights reflected at a plurality of zones in a subject to be photographed, dividing a region between highest and lowest values of the detected light intensities into a plurality of sub-regions, selecting one of the sub-regions and extracting the detected light quantities included in the selected sub-region, calculating a mean value of the extracted light intensities, and determining the exposure in accordance with the mean value of the extracted light quantities.

* * * * *